United States Patent [19]

Nelson et al.

[11] Patent Number: 4,889,882

[45] Date of Patent: Dec. 26, 1989

[54] TETRAMETHYL PIPERIDYL TERMINATED TRIAZINE OLIGOMERIC ESTERS AND AMIDES

[75] Inventors: Richard V. Nelson, Wilmington, Del.; John F. Stephen, West Chester, Pa.

[73] Assignee: ICI Americas Inc., Wilmington, Del.

[21] Appl. No.: 284,583

[22] Filed: Dec. 15, 1988

[51] Int. Cl.[4] .................................................. C08K 5/34
[52] U.S. Cl. ...................................... 524/100; 524/98; 544/113; 544/195; 544/198; 544/209
[58] Field of Search .................. 524/98, 100; 544/198, 544/195, 209, 113

[56] References Cited

U.S. PATENT DOCUMENTS

| Re. 31,261 | 5/1983 | Minagawa et al. | 524/100 |
| 4,348,493 | 9/1982 | Loffelman | 544/209 |
| 4,530,950 | 7/1985 | Raspanti et al. | 524/100 |

Primary Examiner—John Kight
Assistant Examiner—Kriellion Morgan
Attorney, Agent, or Firm—William E. Dickheiser

[57] ABSTRACT

Tetramethylpiperidyl terminated triazine oligomeric esters and amides having a plurality of tetramethyl piperidyl moieties are useful as polymer additives to impart resistance to degradation when exposed to actinic radiation.

17 Claims, No Drawings

TETRAMETHYL PIPERIDYL TERMINATED TRIAZINE OLIGOMERIC ESTERS AND AMIDES

The invention is directed to polymeric compositions which are resistant to degradation and discoloration when exposed to actinic radiation. In particular, it is directed to resins such as polypropylene, polyethylene, etc., which are stabilized with an effective amount of an oligomeric triazine-based compound which contains the 2,2,6,6-tetraalkylpiperidino moiety. The invention is further directed to a novel group of substances which are useful as additives for synthetic polymers which act to retard photodegradation.

Many synthetic organic polymers deteriorate rapidly when exposed to sunlight. To circumvent this rapid degradation many additives have been developed to stabilize these resins against the harmful radiation. Among these additives are UV absorbers such as the hydroxybenzophenones, the hydroxyphenylbenzotriazoles, the organonickel complexes which serve to quench excited states, and most recently the hindered amine light stabilizers (HALS). The HALS possess the 2,2,6,6-tetraalkylpiperidine group that is most commonly substituted in the 4-position and act as radical scavengers, thus inhibiting the degradation process. Among the requirements for a compound to be an effective light stabilizer are the need for it to be compatible with the resin in which it is to incorporated, sufficiently non-volatile so as to remain in the resin during and after processing at elevated temperatures and be resistant to extraction by water.

Although the compounds of the prior art are, in general, effective light stabilizers for synthetic organic polymers, none of these compounds completely satisfy the stabilization requirements of polymers in their wide variety of forms and applications. This is particularly true for those polymeric materials that are used in thin articles, such as fibers and fills. Because of these deficiencies there remains a need for new substances which meet all these requirements more fully.

The present invention is directed to the stabilization of synthetic polymers by the incorporation of an effective amount of a novel triazine compound which possesses the polyalkylpiperidine moiety. The triazine-based HALS of the invention are selected from those described by the general Formula $$R^{12}-\left[T-(B)-\overset{O}{\overset{\|}{C}}-Y-R-Y-\overset{O}{\overset{\|}{C}}-(B)-\underset{A}{N}\right]_m -R^{13} \quad (I)$$

wherein T is the divalent group:

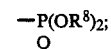

wherein A is:

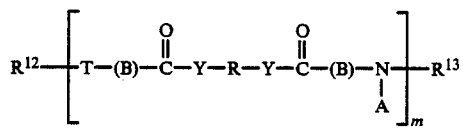

$R^1$ is selected from hydrogen and an alkyl group of 1–5 carbon atoms such as methyl, ethyl, n-propyl, etc., and is preferably hydrogen and methyl and most preferably hydrogen;

$R^2$ is selected from hydrogen, oxyl, hydroxyl, a straight or branched chain alkyl group of 1–18 carbon atoms such as methyl, ethyl, octyl, octadecyl, or 2-ethylhexyl, an alkanoyl group having 2–18 carbon atoms such as acetyl, propanoyl, butanoyl, isopentanoyl, or stearoyl, an alkenyl group of 3–4 carbon atoms, an alkynyl group of 3–6 carbon atoms such as propargyl or 2-butynyl, a cyanomethyl group, an unsubstituted or substituted benzyl group of 7–15 carbon atoms, 3,5-di-tert-butyl-4-hydroxybenzyl, 3-tert-butyl-4-hydroxy-5-methylbenzyl, a group $-CH_2CH(OR^3)-R^4$;

$R^3$ is selected from hydrogen, an aliphatic group of 1–18 carbon atoms, an araliphatic group such as benzyl and phenethyl, and an alkanoyl having 2–18 carbon atoms;

$R^4$ is selected from hydrogen, an alkyl group of 1–16 carbon atoms and phenyl;

X is a group selected from hydrogen, halogen, hydroxyl, straight or branched chain alkyl group having 1–18 carbon atoms, cycloalkyl group having 5–12 carbon atoms, substituted or unsubstituted aryl group having 6–18 carbon atoms, aralkyl group having 7–18 carbon atoms, $-N(R^5)(R^6)$, $-OR^7$, $-SR^7$, or

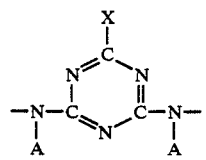

$R^5$ and $R^6$, same or different, can be selected from hydrogen, an alkyl group of 1–18 carbon atoms such as methyl, ethyl, isopropyl, butyl, octyl, dodecyl, and octadecyl, a cycloalkyl group of 5–12 carbon atoms, an aralkyl group of 7–11 carbon atoms such as benzyl and butylbenzyl, a 3–12 carbon alkyl group that may have in the chain a $-O-$ or $-N(R^9)-$ linkage, a hydroxyalkyl group having 2–4 carbon atoms, an acyloxyalkyl group having 3–15 carbon atoms, the group A where $R^1$ and $R^2$ are as described above, or $R^5$ and together with the N-atom to which they are attached may form a heterocyclic ring such as pyrrolidino, piperidino or the ring formed may possess a $-O-$ linkage to form a morpholino group;

$R^7$ is selected from an alkyl group of 1–18 carbon atoms, an alkenyl group of 3–12 carbon atoms, a cycloalkyl group of 5–12 carbon atoms, an aralkyl L group of 7–11 carbon atoms, or an alkyl group of 3–12 carbon atoms which possesses an $-O-$ or $-N(R^9)$ in the chain, or an aryl group of 6–14 carbon atoms such as phenyl, naphthyl, 2,6-dimethylphenyl;

$R^8$ and $R^9$ are selected from an alkyl group having 1-4 carbon atoms such as methyl, ethyl, propyl, etc.;

B is an alkylene group having 1-10 carbon atoms:

Y is selected from —O—, —N(H)—, and )—N($R^{10}$)— where $R^{10}$ represents an alkyl group of 1-20 carbon atoms or the group A;

R is an alkylene group of 2-20 carbon atoms which may be straight-chained or branched, wherein the alkylene group may be interrupted by —O—, —S— or —N($R^{11}$)—, wherein $R^{11}$ is selected from hydrogen, alkyl group having 1-20 carbon atoms, a cycloalkylene group of 5-12 carbon atoms, and a devalent group selected from

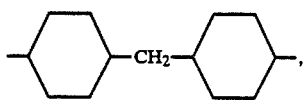

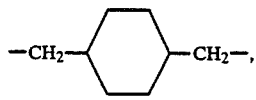

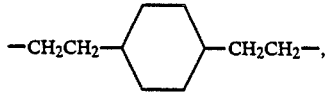

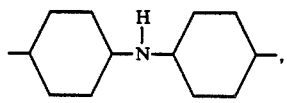

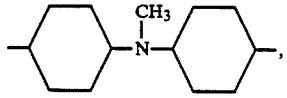

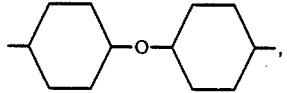

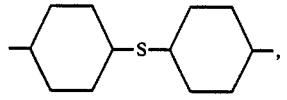

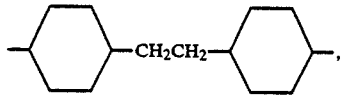

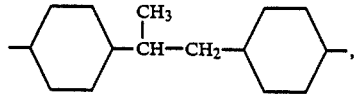

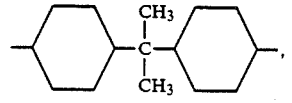

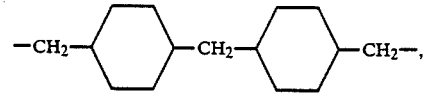

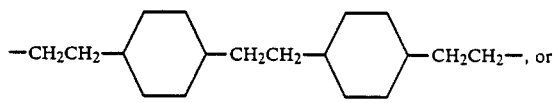

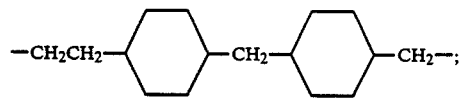

an arylene group of 6-12 carbon atoms, or an aralkylene group of 8-14 carbon atoms;

$R^{11}$ is an alkyl group of 1-18 carbon atoms, a cycloalkylene group of 5-12 carbon atoms or the group A;

$R^{12}$ is the group $X^1$ and is selected from hydrogen and the triazine group

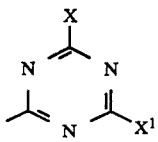

where X is as previously defined and $X^1$ may be the same or different than X.

m is an integer from 1 to 40 and preferably between 2 and 10.

The compounds of Formula (I) can be prepared by the reaction of a substituted triazine of the Formula (II) (See Table of Formulas) where halo indicates Br, Cl, or I with a bis-amine of the general Formula (III) generally in the presence of a solvent such as dioxane, toluene, xylene, or any other solvent suitable for the reaction to occur. Usually the stoichiometry of III to II will be about 1:1. The reaction can be run at a temperature between about 25° C. and 200° C. but is usually and most conveniently run at the reflux temperature of the solvent being used. The reaction may also be carried out in the presence of a base such as hydroxide, carbonate, or an amine such as triethylamine and the like, which serves to scavenge the generated HCl and to permit the reaction to go to completion. Although the use of the base is not necessary for the reaction to proceed it does help to increase the rate at which it reaches completion since the intermediate H-halide addition salts can precipitate from solution. The remaining halogen attached to the triazine ring after initial oligomerization can be removed by reacting the crude product with a desired nucleophilic species such as an amine or alcohol.

The preparation of 2-substituted-4,6-dihalo-1,3,5-triazines of the type described by those of the general Formula (II) is well-known in the literature and prior art. These compounds are generally obtained by the regulated addition of the appropriate amine, alcohol, mercaptan, phosphite or other nucleophilic species, at a lowered temperature such as 0°-5° C. in the presence of an inert solvent such as dioxane or acetone. In the case of the amine addition a scavenging base is used to react with the H-halide with forms during the reaction. This scavenging base can be any of those mentioned above. The product is typically isolated by filtration and drying.

Illustrative examples of compounds of Formula (II) include but are not restricted to the following: 2,4-dichloro-6-tert-butylamino-1,3,5-triazine, 2,4-dichloro- 6-tert-octylamino-1,3,5-triazine, 2,4-dichloro-6-morpholino-1,3,5-triazine, 2,4-dichloro-6-methoxy-1,3,5-triazine, 2,4-dichloro-6-benzylamino-1,3,5-triazine, 2,4-dichloro-6-(2-hydroxyethlyamino)-1,3,5-triazine, 2,4-dibromo-6-cyclohexylamino-1,3,5-triazine, 2,4-dibromo-6-diisopropylamino-1,3,5-triazine, 2,4-dichloro-6-(2-methoxy-ethoxy)-1,3,5-triazine, 2,4-dichloro-6-bis-(2,2,6,6-tetramethyl-4-piperidinylamino)-1,3,5-triazine, 2,4-dichloro-6-ethoxycarbonylmethyleneamino-1,3,5triazine, 2,4,4-dichloro-6-(2-propenyloxy)-1,3,5-triazine, 2,4-dibromo-6-cyclohexyloxy-1,3,5-triazine, 2,4-dichloro-6-methylthio-1,3,5-triazine, 2,4-dichloro-6-dodecylthio-1,3,5-triazine, 2,4-dichloro-6(2-acetoxyethylamino)-1,3,5-triazine, 2,4-dichloro-6-dimethylphosphono-1,3,5-triazine and the like.

The compounds of the Formula (III) can be obtained by the reaction of a compound of the Formula (IV) with a compound H-Y-R-Y-H where B, Y, and R are as previously defined and $R^{14}$ is a lower alkyl group such as methyl or ethyl. This reaction can be performed neat at a temperature between 100° C. and 200° C. using a basic catalyst such as lithium amide, titanium tetraisopropoxide, and the like, with subsequent removal of the generated alcohol. The reaction can also be carried out in an inert solvent such as xylene, toluene, and the like, at or below the reflux temperature of the solvent. Some of the compounds of Formula (IV) have been described in the prior art such as in the patents GB No. 2,136,805 (1983), DE No. 3,512,634 (1986), U.S. Pat. No. 4,578,472, and U.S. Pat. No. 4,670,488.

In general the methods for the synthesis of these compounds include the alkylation of a compound of Formula (V) with the requisite haloacid (or salt) or haloester or via a Michael addition of (V) to the appropriate α,β-unsaturated ester. Other methods which may be used to prepare these compounds include the reductive amination of (V) with the requisite aldehyde such as $OHC(B)CO_2R^{15}$, where $R^{15}$ is hydrogen or lower alkyl or the reversed reductive amination involving Formula (VI) with the requisite amino acid or amino acid ester of Formula (VII).

Illustrative examples of compounds of Formula (III) include but are not restricted to the following: 2,2,6,6-tetramethyl-4-piperidylaminoacetic acid, bis ester with ethylene glycol (m.p. 75°-80° C.), 2,2,6,6-tetramethyl-4-piperidylaminoacetic acid, bis ester with 1,4-butanediol, 3-(2,2,6,6-tetramethyl-4-piperidylamino)-propionic acid, bis ester with 1,6-hexanediol, 1,2,2,6,6-pentamethyl-4-piperidylaminoacetic acid, bis ester with 1,6-hexanediol, 2,2,6,6-tetramethyl-4-piperidylaminoacetic acid, bis ester with 16-hexanediol (m.p. 90°-92° C.), 1,2,2,6,6-pentamethyl-4-piperidylaminoacetic acid, bis ester with 2,2-dimethyl-1,3-propanediol, 2,2,6,6-tetramethyl4-piperidylaminoacetic acid, bis ester with 2,2-dimethyl-1,3-propanediol (m.p. 85°-88° C.), 2,2,6,6-tetramethyl-4-piperidylaminoacetic, bis amide with 1,2-ethanediamine (m.p. 153°-158° C.), 2,2,6,6-tetramethyl-4-piperidylaminoacetic acid, bis amide with 1,6-bis(2,2,2,6-tetramethyl-4-piperidylamino)hexane, 2,2,6,6-tetramethyl-4-piperidylaminoacetic acid, bis ester with 2,2'-dihydroxyethylether, 2-methyl-3-(2,2,6,6-tetramethyl-4-piperidylamino) propionic acid, bis ester with ethylene glycol, 4-(2,2,6,6-tetramethyl-4-piperidyl)-butanoic acid, bis ester with 2,2-dimethyl-1,3-propanediol, 2,2,6,6-tetramethyl-4-piperidylaminoacetic acid, bis ester with N,N-di(2-hydroxyethyl)-4-amino-2,2,6,6-tetramethylpiperidine, 2,2,6,6-tetramethyl-4-piperidylaminoacetic acid, bis ester with 1,4-cyclohexanedimethanol, 3-(2,2,6,6-tetramethyl-4-piperidylamino)propionic acid, bis amide with 1,6-hexanediamine, 3-(2,2,6,6-tetramethyl-4-piperidylamino)-propionic acid, bis ester with 2,2-dimethyl-1,3-propanediol, (m.p. 128°-130° C.), 11-(2,2,6,6-tetramethyl-4-piperidylamino)undecanoic acid, bis ester with ethylene glycol, 6-(2,2,6,6-tetramethyl-4-piperidylamino)hexanoic acid, bis ester with 2,2,-dimethyl-1,3-propanediol, and the like.

The 4-aminopolyalkylpiperidines used as intermediates for conversion to compounds of the invention are known from U.S. Pat. No. 3,684,765 and in general are prepared by the reduction amination of the corresponding ketone using either ammonia or the amine of interest.

The 4-oxopiperidines of Formula (VI) can be prepared by the reaction of ammonia with an aliphatic ketone. The reaction of ammonia with acetone to yield triacetoneamine is well known and various processes exist in the art for its manufacture. The reaction of ammonia with methyl ethyl ketone has been described by W. Traube in Chem. Ber. 41,777 (1908).

Compounds of the Formula (VI) that have other alkyl substituents in the 2-position and the 6-position can be prepared in a two-step process following the procedures outlined in Helv. Chim. Acta 30,1114 (1947) and Monatsh. Chem. 88, 464 (1957), followed by hydrolysis of the resulting pyrimidine.

In the examples of the invention where $R^2$ is other than hydrogen the additional derivatization can be carried out most readily on the compound of Formula (VI). In general, the introduction of $R^2$ is readily accomplished by performing the appropriate transformation such as alkylation or oxidation on the parent N-H compound and then introduce the 4-amino substituent by reductive amination.

The reductive amination can be carried out in the manner that has been well described in the prior art and primary literature. In general any catalyst that is commonly used in catalytic hydrogenation reactions can be used. Preferred catalysts include palladium on carbon and platinum on carbon. The reaction is normally run in the presence of a solvent. Suitable solvents as wall as others include methanol and ethanol. The hydrogenation is usually carried out at a hydrogen pressure of 1-10 atmospheres and at a temperature necessary to achieve the reduction. In general the reduction can be achieved at ambient temperature but in some instances up to about 100° C. may be used.

The introduction of an alkyl, alkenyl, alkynyl, and aralkyl can be achieved by reaction of the initially prepared ketone of Formula (VI) or the derivatized triazine of Formula (I) which contain the free N-H of the piperidine with the suitable halide. Examples of suitable halides include methyl iodide, methyl chloride, ethyl bromide, dodecyl chloride, octadecyl chloride, allyl bromide, methallyl chloride, butenyl chloride, propargyl chloride, benzyl chloride, phenethyl bromide, and epichlorohydrin. The generated hydrogen halide can be scavenged by the addition of an inorganic base such as carbonate or hydroxide or by the addition of an organic amine such as triethylamine to the reaction mixture.

The introduction of an alkanoyl or an alkenoyl group can be performed by acylation of the N—H group using the suitable acid halide or, when convenient, the acid anhydride. If the acid halide is used the generated hydrogen halide can be scavenged in the same manner as stated previously. Examples of such groups are acetyl chloride, acetic anhydride, propionic anhydride, hexanoyl chloride, dodecanoyl chloride, and octadecanoyl chloride.

For the introduction of the group —CH$_2$—CH—(O—R$^3$)—R$^4$ the substituent can be introduced by reaction of the parent N-H compound with the corresponding alkylene oxide such as ethylene oxide, propylene oxide and styrene oxide. The resulting hydroxy compound can be acylated in the manner commonly known in the art using the suitable acid halide and can be alkylated by formation of the alkoxide and reaction with the desired alkyl halide.

For R$^2$ as the oxyl group of hydroxyl group the parent N—H compound can be treated with an oxidizing agent such as hydrogen peroxide in the presence of a catalyst like sodium tungstate or with a percarboxylic acid like metachloroperbenzoic acid, with subsequent reduction of the oxyl by catalytic hydrogenation if the hydroxyl is desired.

The compounds of this invention are effective light stabilizers for synthetic organic polymers. The following examples are offered to demonstrate but not limit the scope of the invention: 2,4-dichloro-6-t-butylamino-1,3,5-triazine, oligomer with 2,2,6,6-tetramethyl-4-piperidylaminoacetic acid, bis ester with 2,2,-dimethyl-1,3-propanediol; 2,4-dichloro-6-tert-octylamino-1,3,5-triazine, oligomer with 2,2,6,6-tetramethyl-4-piperidylaminoacetic acid, bis ester with 2,2-dimethyl-1,3-propanediol; 2,4-dichloro-6-morpholino-1,3,5-triazine, oligomer with 2,2,6,6-tetramethyl-4-piperidylaminoacetic acid, bis ester with 2,2-dimethyl-1,3-propanediol; 2,4-dichloro-6-tert-octylamino-1,3,5-triazine, oligomer with 3-(2,2,6,6-tetramethyl-4-piperidylamino)propionic acid, bis ester with 2,2-dimethyl-1,3-propanediol; 2,4-dichloro-6-morpholino-1,3,5-triazine, oligomer 2,2,6,6-tetramethyl-4-piperidylaminoacetic acid, bis ester with 1,6-hexanediol; 2,4-dichloro-6-morpholino-1,3,5-triazine, oligomer with 3-(2,2,6,6-tetramethyl-4-piperidylamino)propionic acid, bis ester with ethylene glycol; 2,4-dichloro-6-tert-butylamino-1,3,5-triazine, oligomer with 2,2,6,6-tetramethyl-4-piperidylaminoacetic acid, bis ester with ethylene glycol; 2,4-dichloro-6-methoxy-1,3,5-triazine, oligomer with 3-(1,2,2,6,6-pentamethyl-4-piperidylamino)propionic acid, bis ester with 2,2-dimethyl-1,3-propanediol; 2,4-dichloro-6-diallylamino-1,3,5-triazine, oligomer with 2,2,6,6-tetramethyl-4-piperidylaminoacetic acid, bis ester with ethylene glycol; 2,4-dichloro-6-morpholino-1,3,5-triazine, oligomer with 2,2,6,6-tetramethyl-4-piperidylaminoacetic acid, bis amide with 1,2-diaminoethane, 2,4-dichloro-6-dodecylthio1,3,5-triazine, oligomer with 1,2,2,6,6-pentamethyl-4-piperidylaminoacetic acid, bis amide with 1,6-hexanediamine; 2,4-dichloro-6-morpholino-1,3,5-triazine, oligomer with 4-(2,2,6,6-tetramethyl-4-piperidylamino)butanoic acid, is ester with 1,6-hexanediol; 2,4-dichloro-6-(2,2,6,6-tetramethyl-4-piperidyl)-amino-1,3,5-triazine, oligomer with 5-(2,2,6,6-tetramethyl-4-piperidylamino)pentanoic acid, bis ester with ethylene glycol: 2,4-dichloro-6-tert-octylamino-1,3,5-triazine, oligomer with 2,2,6,6-tetramethyl-4-piperidylaminoacetic acid, bis ester with 1,6-hexanediol; and the like.

The compounds of this invention are effective light stabilizers for synthetic organic polymers. In addition to their effective light stabilizing properties some of the compounds of this invention also exhibit excellent thermal stabilizing performance. Among the synthetic organic polymers which can be stabilized by the compounds of this invention are the polyolefins which include homopolymers of olefins like polyethylene, both high- and low-density polyethylene, polypropylene, polybutadiene, polystyrene, and the like; and copolymers of olefins with other ethylenically unsaturated monomers such as ethylenepropylene copolymer, ethylene-butylene copolymer, ethylene-vinyl acetate copolymer, styrenebutadiene copolymer and the like: terpolymers such as acrylonitrile-butadiene-styrene and the like; polyvinyl chlorides, polyvinylidene chlorides, copolymers of vinyl chloride and vinylidene chloride with vinyl acetate or other ethylenically unsaturated monomers; polyacetals such as polyoxymethylene and polyoxyethylene, polyesters such as polyethylene terephthalate; polyamides such as polyamide 6, polyamide 6,6, polyamide 6,10; polyurethanes and polymers derived from unsaturated acids and derivatives thereof; polycarbonates; polyacrylates and polymethacrylates, polyacrylic amides and polyacrylonitrile, as well as copolymers of acrylic acid and one or more of its derivatives with a melamine-formaldehyde resin.

Of particular importance among these groups of polymers is the stabilization of polyolefins. The compounds of this invention are excellent for their stabilization in an amount ranging from 0.01 to 5.0% by weight based on the weight of the polymer to be stabilized. Preferably they may be used in an amount between 0.05 and 1% by weight.

The compounds of the invention may also be used in conjunction with other stabilizers for the preparation of stabilized resin compositions. Among these other additives may be antioxidants, supplemental light stabilizers such as UV absorbers or other hindered amines, metal deactivators, etc., pigments, colorants, fillers, flame retardants, antistatic agents, and the like.

Suitable antioxidants include those of the hindered phenol type such as 2,6-di-t-butyl-p-cresol; 2,4,6-tri-t-butyl-phenol; 2,2'-thiobis(4-methyl-6-t-butylphenol) octadecyl-3-(3',5'-di-t-butyl-4'-hydroxyphenyl)propionate; pentaerythrityl tetrakis(3-(3,5-di-t-butyl-4-hydroxyphenyl) propionate); 1,3,5tris(3',5'-di-t-butyl-4'-hydroxybenzyl)isocyanurate; 1,3,5-tris-(3',5'-di-t-butyl-4'-hydroxybenzyl) isocyanurate; 1,3,5-tris(2,6-dimethyl-4-t-butyl-3hydroxybenzyl) isocyanurate; 3,5-di-t-butyl-4-hydroxy hydrocinnamic acid triester with 1,3,5-tris(2-hydroxyethyl)-s-triazine-2,4,6-(1H,3H,5H) trione; esters of thiodipropionic acid such as dilaurylthiodipropionate and distearylthiodipropionate, etc.; phosphites such as triphenyl phosphite, trinonylphenyl phosphite, distearyl pentaerythrityl diphosphite, diphenyldecyl phosphite, tris-(2,4,-di-t-butylphenyl)phosphite, bis(2,4-di-t-butylphenyl)pentaerythritol diphosphite, etc.; supplemental light stabilizers such as those of the benzotriazole class including 2-(2'-hydroxy-5'-toctylphenyl)benzotriazole; 2-(2'-hydroxy-3',5'-di-t-butylphenyl)-5-chlorobenzotriazole; 2-(2'-hydroxy-5'-di-t-methylphenyl)benzotriazole; 2-(2'-hydroxy-3'-t-butyl-5'-methylphenyl)benzotriazole; 2-(2'-hydroxy-3',5'-di-t-amylphenyl)benzotriazole; those of the hydroxybenzophenone type such as 2-hydroxy-4-methoxybenzophenone; 2-hydroxy-4-octyloxybenzophenone; hindered phenols such as n-hexaadecyl-3,5-di-t-butyl-4-hydroxybenzoate and 2',4'-di-t-butylphenol-3,5-di-t-butyl-4-hydroxy-benzoate;

Metal complexes such as nickel complexes of 2,2'-thiobis-(4-ter-octylphenol), nickel dibutyl dithiocarbamate; nickel salts of 4-hydroxy-3,5-di-t-butylbenzylphosphonic acid monoalkyl esters where alkyl is methyl, ethyl, etc., and methylphenylundecylketoneoxime.

Other examples of suitable supplemental light stabilizers may be found in U.S. Pat. Nos. 3,488,290 and 3,496,134.

The following examples are given to illustrate the present invention and are not meant to limit the nature or scope of the invention in any manner. NMR analysis of each example yielded a spectrum consistent with the oligomeric mixture expected. FAB-MS analysis of the examples yielded values of n in the range of 1-8.

EXAMPLE 1

A mixture of 2,4-dichloro-6-morpholino-1,3,5-triazine (1.52 g, 6.48 mmol) and 2,2,6,6-tetramethyl-4-piperidylaminoacetic acid, bis ester with ethylene glycol (2.95 g, 6.48 mmol) was heated at reflux in dioxane (25 ml) for about 18 hrs. Upon completion of the reaction the dioxane was removed and the residue was dissolved in methylene chloride and washed with dilute sodium hydroxide and then with water. The solution was then dried and concentrated to yield a light yellow viscous residue. Manipulation yielded a beige solid (mp 110°-114° C.) weighing about 4.0 g.

EXAMPLE 2

In a manner essentially identical to the procedure stated for the synthesis of Example 1 was prepared the oligomeric mixture derived from 2,4-dichloro-6-t-octylamino-1,3,5-triazine (1.97 g) and 2,2,6,6-tetramethyl-4-piperidylaminoacetic acid, bis ester with neopentyl glycol (3.55 g). After workup manipulation the product was obtained as an off-white foamy solid (4.37 g) having a melting point of 47°-54° C.

EXAMPLE 3

To a sample of the product of Example 2 (5.0 g), prepared in a analogous manner to that stated above, was added 30 ml of toluene and about 2 g of t-octylamine. The mixture was refluxed for 18 hours, then coated and partitioned with water and brine. Backwashing, drying (Na$_2$SO$_4$) and concentration yielded a yellow residue. Vacuum treatment yielded a crunchy foam (3.8 g) having a melting point of 59°-62° C.

EXAMPLE 4

In a manner identical to that of Example 1 was prepared the oligomeric mixture derived from 2,4-dichloro-6-t-butylamino-1,3,5-triazine (1.71 g) and 2,2,6,6-tetramethyl-4-piperidylaminoacetic acid, bis ester with neopentyl glycol (3.85 g). Upon workup and isolation the product was isolated as a beige foam weighing 2.97 g and had a collapsing temperature of 50°-55° C.

EXAMPLE 5

In the same manner as Example 4 was prepared the oligomeric mixture with the substitution of 2,4-dichloro-6-morpholino-1,3,5-triazine for 2,4-dichloro-6-morpholino-1,3,5-triazine. The quantities of reactants used were 1.78 g of the above-mentioned triazine and 3.77 g of the bis ester. Upon workup after 6 hours at reflux the product was isolated as a beige foam weighing 3.42 g and had a collapsing temperature of 50°-55° C.

EXAMPLE 6

In the manner of Example 1 was prepared the oligomeric mixture derived from 2,4-dichloro-6-morpholino-1,3,5-triazine (1.53 g) and 2,2,6,6-tetramethyl-4-piperidylaminoacetic acid, bis amide with ethylenediamine (2.94 g). After about 18 hours at reflux and partitioning between CH$_2$Cl$_2$ and water, the organic solution was dried and concentrated to yield 3.93 g of a beige foam which collapsed at 55°-60° C.

EXAMPLE 7

Similar to that of Example 6 was prepared the oligomeric mixture derived from 2,4-dichloro-6-t-butylamino-1,3,5-triazine (1.10 g) and 2,2,6,6-tetramethyl-4-piperidylaminoacetic acid, bis amide with ethylenediamine (2.26 g). In this example powdered K$_2$CO$_3$ (1.38 g) was used in the reaction rather than performing a caustic wash during workup. As in Example 6 the resulting product from workup was a beige foam (2.84 g) which collapsed at 55°-60° C.

EXAMPLE 8

In the manner of Example 7 was prepared the oligomeric mixture derived from 2,4-dichloro-6-morpholino-1,3,5-triazine (1.40 g) and 2,2,6,6-tetramethyl-4-piperidylaminoacetic acid, bis amide with 1,6-hexanediamine (3.08 g). In this example K$_2$CO$_3$ (1.64 g) was used also. Upon completion of the reaction the mixture was worked up as Example 7 to yield 4.16 g of the product having a softening point of 90°-93° C.

EXAMPLE 9

A mixture of 2,4-dichloro-6-t-octyl-amino-1,3,5-triazine (1.9 g, 6.85 mmol) and 3-(2,2,6,6-tetramethyl-4-piperidylamino)-propionic acid, bis ester with 2,2-dimethyl-1,3-propanediol (3.6 g, 6.85 mmol) was heated at reflux in dioxane (25 ml) for about 18 hrs. Upon completion of the reaction the dioxane was removed. The residue was dissolved in methylene chloride and washed with dilute aqueous sodium hydroxide and then with water. The solution was dried and concentrated to yield a yellow viscous residue.

EXAMPLES 10-14

In order to further illustrate the effectiveness of the above-described compounds as light stabilizers the materials described by Examples 2-5 were each incorporated into a commercially available polypropylene resin manufactured by Hercules Corporation as Pro-Fax 6301 Polypropylene Resin. The light stabilizers were incorporated into the polypropylene by solvent blending methylene chloride at a concentration of 0.25% by weight of the total resin composition. A primary antioxidant (stearyl β-(3,5-di-t-butyl-4-hydroxyphenyl) propionate) was used at a level of 0.2%. The resin was then extruded at 200° C. and compression molded at 6,000 psi at 188° C. to produce films having a thickness of 5 mils. A control film was also produced by an identical procedure with the light stabilizer omitted. Each film was exposed to a Xenon Arc in an Atlas Weather-o-Meter until the IR carbonyl increased by 0.5, which is considered to be the failure point.

TABLE 1

| Example # | Stabilizer | Hrs. to Failure |
|---|---|---|
| 10 | Control | 400 |
| 11 | Compound 2 | 3050 |

TABLE 1-continued

| Example # | Stabilizer | Hrs. to Failure |
|---|---|---|
| 12 | Compound 3 | 2300 |
| 13 | Compound 4 | 3625 |
| 14 | Compound 5 | 3290 |

TABLE OF FORMULAS

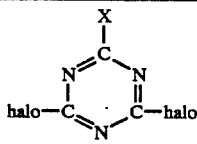  (II)

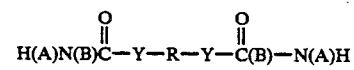  (III)

$HAN(B)CO_2R^{14}$      (IV)
$A-NH_2$      (V)

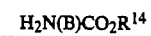  (VI)

$H_2N(B)CO_2R^{14}$      (VII)

What is claimed is:

1. A compound of the Formula I

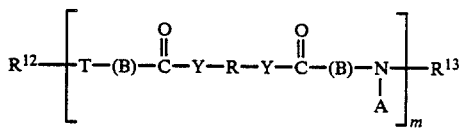

wherein T is the divalent group:

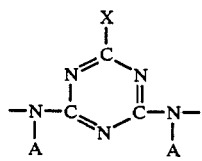

wherein A is:

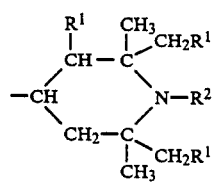

$R^1$ is selected from hydrogen and an alkyl group 1-5 carbon atoms, $R^2$ is selected from hydrogen, oxyl, hydroxyl, a straight or branched alkyl group 1-18 carbon atoms, an alkanoyl group having 2-18 carbon atoms, an alkenyl group of 3-4 carbon atoms, an alkenoyl group of 3-6 carbon atoms, an alkynyl group of 3-6 carbon atoms, a cyanomethyl group, benzyl group of 7-15 carbon atoms and a group $-CH_2CH(OR^3)-R^4$, $R^3$ is selected from hydrogen, an aliphatic group of 1-18 carbon atoms, an araliphatic group and an alkanoyl group having 2-18 carbon atoms;

$R^4$ is selected from hydrogen, an alkyl group of 1-16 carbon atoms and phenyl;

X is a group selected from hydrogen, halogen, hydroxyl, alkyl group having 1-18 carbon atoms, cycloalkyl group having 5-12 carbon atoms, aryl group having 6-18 carbon atoms, aralkyl group having 7-18 carbon atoms, $-N(R^5)(R^6)$, $-OR7$, $-SR^7$, or

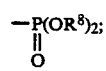

$R^5$ and $R^6$, same or different, can be selected from hydrogen, an alkyl group of 1-18 carbon atoms, a cycloalkyl group of 5-12 carbon atoms, an aralkyl group of 7-11 carbon atoms, an alkyl group having 3-12 carbon atoms that may have in the chain an $-O-$ or $-N(R^9)-$ linkage, a hydroxyalkyl group having 2-4 carbon atoms, an acyloxyalkyl group having 3-15 carbon atoms, the group A, or $R^5$ and $R^6$, together with the N-atom to which they are attached form a heterocyclic ring selected from the group consisting of pyrrolidino, piperidino, and those containing an $-O-$ linkage to form a morpholino group;

$R^7$ is selected from an alkyl group of 1-18 carbon atoms, an alkenyl group of 3-12 carbon atoms, a cycloalkyl group of 5-12 carbon atoms, an aralkyl group of 7-11 carbon atoms, an alkyl group of 3-12 carbon atoms which possesses an $-O-$ or $-N(R^9)$ in the chain, and aryl group of 6-14 carbon atoms;

$R^8$ and $R^9$ are selected from an alkyl group having 1-4 carbon atoms;

B is an alkylene group having 1-10 carbon atoms;

Y is selected from $-O-$, $-N(H)-$, and $-N(R^{10})-$ where $R^{10}$ represents an alkyl group of 1-20 carbon atoms or the group A, R is selected from an alkylene group of 2-20 carbon atoms which may be straight-chained or branched wherein the alkylene may be interrupted by $-O-$ $-S-$, or $-N(R^{11})-$ wherein $R^{11}$ is selected from hydrogen, an alkyl having 1-20 carbon atoms, the group A, a cycloalkylene group 5-12 carbon atoms, a divalent group selected from

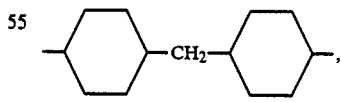

-continued

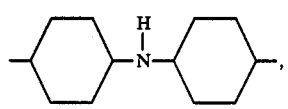

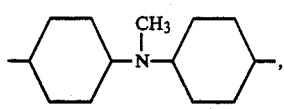

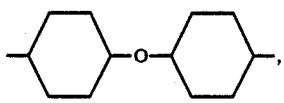

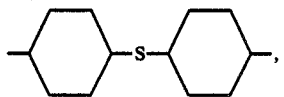

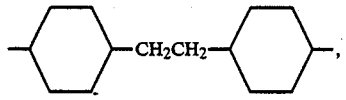

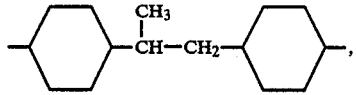

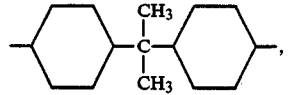

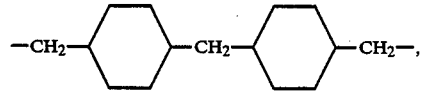

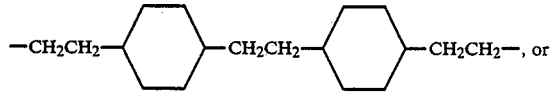

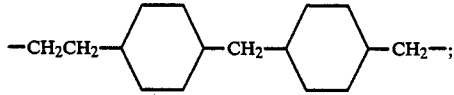

a group selected from an arylene group of 6-12 carbon atoms, or an aralkylene group of 8-14 carbon atoms, $R^{11}$ is an alkyl group of 1-18 carbon atoms, a cycloalkylene group of 5-12 carbon atoms or the group A, $R^{12}$ is the group $X^1$ and $R^{13}$ is selected from hydrogen and the triazine group

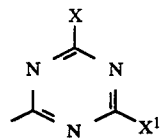

where X is a previously defined and $X^1$ may be the same or different than X, and m is an integer from 1 to 40.

2. A compound of claim 1 wherein $R^1$ is hydrogen.
3. A compound of claim 2 wherein B is methylene.
4. A compound of claim 3 wherein Y is —O— or —NH—.
5. A compound of claim 4 wherein m is 1 to 10.
6. A compound of claim 2 wherein B is selected from methylene and ethylene and $R^2$ is hydrogen.
7. A compound of claim 6 wherein X is the tert-butylamino group, Y is —O—, and R is the 2,2-di-methyl-1,3-propylene group.
8. A compound of claim 6 wherein X is the tert-octylamino group, Y is —O—, B is methylene and R is the 2,2-dimethyl-1,3-propylene group.
9. A compound of claim 6 wherein X is the morpholino group, Y is —O—, B is methylene and R is the 2,2-dimethyl-1,3-propylene group.
10. A compound of claim 6 wherein X is the morpholino group, Y is —NH— and R is the 1,6-hexylene group.
11. A compound of claim 6 wherein X is morpholino, Y is —O— and R is the 1,2-ethylene group.
12. A compound of claim 6 wherein X is tert-butylamino, Y is —NH—, and R is the 1,2-ethylene group.
13. A compound of claim 6 wherein X is tert-octylamino, B is ethylene, Y is —O— and R is the 2,2-dimethyl-1,3-propylene group.
14. A compound of claim 6 wherein X is morpholino, B is methylene, Y is —NH—, and R is the 1,2-ethylene group.
15. A synthetic polymer composition stabilized against light-induced degradation comprising an organic polymer normally subject to deterioration by light and from 0.01-5% by weight of a compound of the general formula of claim 1.
16. A composition of claim 15 wherein the organic polymer is a polyolefin homopolymer or copolymer.
17. A composition of claim 16 wherein said organic polymer is a homo- or copolymer of propylene.

* * * * *